United States Patent [19]
Hughes

[11] Patent Number: 5,840,926
[45] Date of Patent: Nov. 24, 1998

[54] PHOTOCHROMIC ARTICLES

[75] Inventor: Frank J. Hughes, Edina, Minn.

[73] Assignee: Vision-Ease Lens, Inc., Brooklyn Center, Minn.

[21] Appl. No.: 895,655

[22] Filed: Jul. 17, 1997

Related U.S. Application Data

[63] Continuation of Ser. No. 477,137, Jun. 7, 1995, abandoned.

[51] Int. Cl.$^6$ .......................... G02B 5/23; C07D 311/78; C07D 405/10
[52] U.S. Cl. .......................... 549/384; 252/586; 351/163
[58] Field of Search .......................... 549/384; 252/586; 351/163

[56] References Cited

U.S. PATENT DOCUMENTS

| | | | |
|---|---|---|---|
| 3,567,607 | 3/1971 | Saunders et al. | 204/159.2 |
| 4,818,096 | 4/1989 | Heller et al. | 351/163 |
| 4,931,221 | 6/1990 | Heller | 252/586 |
| 5,066,818 | 11/1991 | Gemert et al. | 549/389 |
| 5,106,998 | 4/1992 | Tanaka et al. | 549/331 |
| 5,238,981 | 8/1993 | Knowles | 524/110 |
| 5,244,602 | 9/1993 | Van Gemert | 252/589 |
| 5,274,132 | 12/1993 | VanGemert | 549/389 |
| 5,464,567 | 11/1995 | Knowles et al. | 252/586 |

*Primary Examiner*—Deborah C. Lambkin
*Attorney, Agent, or Firm*—Kinney & Lange, P.A.

[57] ABSTRACT

A photochromic article that includes a host material and a photochromic amount of a naphthopyran compound, the naphthopyran compound represented by the formula:

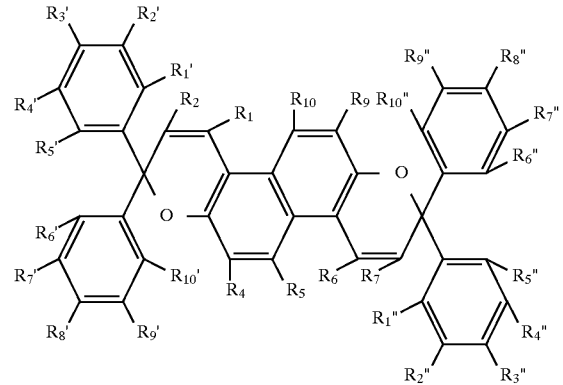

wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the following group: a stable organic radical, a heterocyclic group, halogen, a nitrogen-substituted group, and a nitrogen-substituted ring compound.

23 Claims, No Drawings

PHOTOCHROMIC ARTICLES

This is a continuation of application Ser. No. 08/477,137, filed Jun. 7, 1995, abandoned.

BACKGROUND OF THE INVENTION

The present invention generally relates to articles that are made of photochromic compounds. More specifically, the present invention relates to articles that are made of photochromic naphthopyran compounds.

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the compound is isolated from the ultraviolet radiation, such as by placing the compound in a dark room.

Various products, including optical lenses, incorporate the principal of photochromism. For example, photochromic compounds, such as naphthopyrans, are incorporated into plastic ophthalmic lenses to effect color changes in the plastic lenses when the lenses are exposed to particular lighting conditions. Additionally, different photochromic compounds may be blended to create a color effect that is different from the respective color effects of the individual photochromic compounds. As an example, a first photochromic compound that turns orange or red when activated by light and a second photochromic compound that turns blue when activated by light may be blended to form a photochromic mixture that produces a shade of gray when activated by light.

Several types of photochromic compounds have been reported which exhibit changes in color when exposed to ultraviolet light. One particular class of photochromic compounds includes the 3,3-disubstituted naphthopyrans. One specific group of 3,3-disubstituted naphthopyran of interest includes the 3H-naphtho[2,1b]pyrans. The color response of the 3H-naphtho[2,1b]pyrans to ultraviolet light extends to purple, red, orange or yellow, depending upon the composition and structure of the particular 3H-naphtho[2,1b]pyran. A general expression of the 3H-naphtho[2,1b]pyrans is provided in graphical formula I:

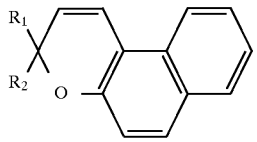

I where $R_1$ and $R_2$ are substituents attached to the pyran ring at the position indicated.

Several photochromic compounds are described in U.S. Pat. No. 3,567,605 to Becker. The Becker patent describes chromenes and chromene derivatives which are photochromic at relatively low temperatures. The patent also describes chromenes and chromene derivatives which are photochromic at room temperature, such as diphenyl-3H-naphtho[2,1b]pyran, where $R_1$ and $R_2$ of formula I are each unsubstituted phenyl groups.

Additional photochromic compounds are described in U.S. Pat. No. 4,931,221 to Heller et al. One type of photochromic compound described in Heller generally has the form of graphical formula I with $R_1$ and $R_2$ being cyclopropyl radicals and with any of various substituents included on the naphtho portion of the naphthopyran rings. Heller reports a larger bathochromic shift in the visible spectrum of 3H-naphtho[2,1b]pyrans that include the cyclopropyl radicals, as compared to 3H-naphtho[2,1b]pyrans that include alkyl groups or a spirocycloalkyl group in place of the cyclopropyl radicals.

Other photochromic compounds are described in U.S. Pat. No. 5,066,818 to Gemert et al. One photochromic compound class described in Gemert generally meets graphical formula I with one of $R_1$ and $R_2$ being a substituted phenyl radical, with one of $R_1$ and $R_2$ being either a substituted or unsubstituted phenyl radical, and with various substituents included on the naphtho portion of the naphthopyran rings. Gemert lists various non-aryl groups as potential substituents of the phenyl radicals of $R_1$ and $R_2$. Gemert reports a range of decolorization rates associated with the 3H-naphtho[2,1b]pyrans that include the phenyl radicals as $R_1$ and $R_2$.

Additional photochromic compounds are described in U.S. Pat. No. 5,106,998 to Tanaka et al. Tanaka describes compounds in which $R_1$ and $R_2$ of graphical formula I are alkyl groups. Tanaka reports several fade times and maximum absorption wavelengths associated with various 3H-naphtho[2,1b] pyrans that include the alkyl radicals as $R_1$ and $R_2$ in formula I.

U.S. Pat. No. 5,238,981 to Knowles teaches a 3H-naphtho[2,1b] pyran compound in which $R_1$ and $R_2$ of graphical formula I are each selected from a group of organic radicals that includes phenyl and naphthyl. The organic radicals placed at $R_1$ and $R_2$ are either substituted or unsubstituted. Potential substituents of substituted organic radicals placed at $R_1$ and $R_2$, provided that one of the organic radicals placed at $R_1$ and $R_2$ is a phenyl group, include various non-aryl groups. Various potential substitutions on the naphtho portion of the naphthopyran ring are taught, including an 8-methoxy substitution. Knowles states that the number eight carbon atom substitutions, such as the 8-methoxy substitution, cause a bathochromic shift in the visible spectrum associated with activated forms of the 3H-naphtho[2,1b]pyrans and in the ultraviolet spectrum of unactivated forms of the 3H-naphtho[2,1b]pyrans.

Additional photochromic compounds are described in U.S. Pat. No. 5,244,602 to Van Gemert. Van Gemert describes 3H-naphtho[2,1b]pyrans in which $R_1$ and $R_2$ of graphical formula I are each phenyl, naphthyl, various heterocyclic groups, and certain non-aryl groups. Van Gemert also discusses substitution of various non-aryl substituents into any phenyl, naphthyl, heterocyclic, and non-aryl groups placed at $R_1$ and $R_2$. Van Gemert also states that certain substitutions at the number 5 carbon on the naphtho ring causes a bathochromic shift of the absorption maximum of the 3H-naphtho[2,1b]pyrans.

U.S. Pat. No. 5,274,132 to Van Gemert describes certain 3H-naphtho[2,1b]pyrans in which $R_1$ of graphical formula I is a phenyl group, a naphthyl group, a furyl group, or a thienyl group and in which $R_2$ of graphical formula I is an arylalkenyl radical. Van Gemert describes a bathochromic shift associated with the 3H-naphtho[2,1b]pyrans that include the arylalkenyl radical, relative to certain other naphthopyrans disclosed in U.S. Pat. No. 3,567,605.

SUMMARY OF THE INVENTION

The present invention encompasses a photochromic article that includes a host material and a photochromic amount of a naphthopyran compound that is represented by the formula:

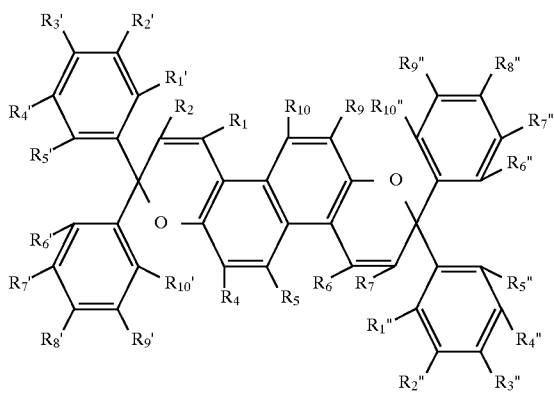

wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the following group: a stable organic radical, a heterocyclic group, halogen, a nitrogen-substituted group, and a nitrogen-substituted ring compound.

DETAILED DESCRIPTION OF THE PREFERRED EMBODIMENTS

Novel photochromic compounds have been discovered which enable high wavelength activation and deep coloring. On activation, the novel photochromic compounds produce colors that are capable of being blended with blue-producing photochromic compounds to form photochromic blends that produce remarkably pleasing gray colors when the blends are activated by ultraviolet radiation. Furthermore, the novel photochromic compounds have acceptable fade rates and may therefore be desirably incorporated into a variety of photochromic articles.

Novel naphthopyran compounds of the present invention may be represented by graphic formula II as follows:

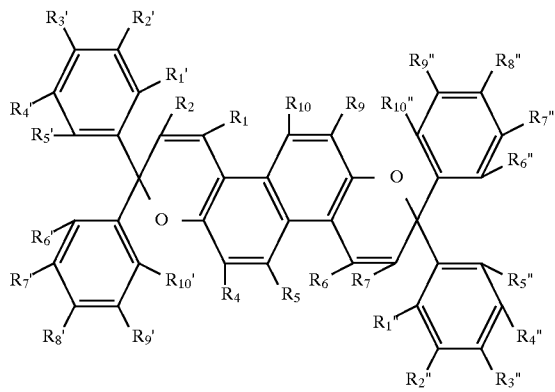

For purposes of the present application, including the description and the claims, it is to be understood that graphical formula II includes all structural isomers of the compounds represented by graphical formula II.

A variety of substituents may be placed on the pyran portion and the naphtho portion of the naphthopyran rings. For example, the positions represented in graphic formula II by $R_1$, $R_2$, $R_4$, $R_5$, $R_6$, $R_7$, $R_9$, and $R_{10}$ may each be filled with hydrogen; a stable organic radical, such as alkyl, alkoxy, unsubstituted or substituted phenyl, unsubstituted or substituted phenoxy, naphthyl, naphthoxy, cycloalkyl, furyl, alkoyl, alkoyloxy, aroyl, or aroyloxy; a heterocyclic group; halogen; a nitrogen-substituted group, such as amino, dialkylamino, or nitro; or a nitrogen-substituted ring compound, such as morpholino, piperidino, or piperazino. Also in graphic formula II, $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the following: a stable organic radical, such as alkyl, alkoxy, unsubstituted or substituted phenyl, unsubstituted or substituted phenoxy, naphthyl, naphthoxy, cycloalkyl, furyl, alkoyl, alkoyloxy, aroyl, or aroyloxy; a heterocyclic group; halogen; a nitrogen-substituted group, such as amino, dialkylamino, or nitro; and a nitrogen-substituted ring compound, such as morpholino, piperidino, or piperazino.

The naphthopyran compounds represented by graphic formula II are derivatives of 3,3-aryl-disubstituted-aryl chromenes. These naphthopyran compounds exhibit a surprising and highly desirable bathochromic shift of the maximum activated wavelength. The bathochromic shift exhibited by the inventive naphthopyran compounds provide photochromic species which turn orange, reddish-orange or purple when activated by a source of ultraviolet radiation, such as solar radiation or light radiated from a mercury or xenon lamp.

It has been found desirable to produce photochromic compounds with maximum activated wavelengths approaching 500 nanometers. Photochromic compounds with maximum activated wavelengths near 500 nanometers change from original states of color to deep shades of orange, reddish-orange or red when activated by ultraviolet light. The colored forms of the activated photochromic compounds fade to the original, unactivated colored states at ambient temperatures when isolated from the ultraviolet light. Photochromic compounds that turn deep shades of orange, reddish orange, or red when activated are hereinafter referred to as "intense photochromes" for purposes of this disclosure only.

The inventive naphthopyrans represented by graphical equation II, especially the intense photochromes, exhibit a deep color and a larger bathochromic shift in the visible spectrum of the activated form, as compared to existing naphthopyrans. Indeed, the inventive naphthopyrans represented by graphical equation II, especially the intense photochromes, approach, and in some cases attain, a maximum activated wavelength of 500 nanometers and exhibit deep shades of orange, reddish orange, or purple when activated. Also, the inventive naphthopyrans represented by graphical equation II have an acceptable fade characteristic.

The inventive intense photochromes may be blended with one or more other photochromic compounds of different maximum activation wavelengths from that of the inventive intense photochromes to make photochromic mixtures. Preferably, the other photochromic compounds turn colors other than orange, reddish orange and purple when activated with ultraviolet light. In one embodiment, one or more of the inventive intense photochromes is preferably blended with another photochromic compound which has a different maximum activation wavelength and which turns blue when activated with ultraviolet light to make the photochromic mixture.

It has been discovered that photochromic mixtures that include the inventive intense photochromes and blue-turning photochromic compounds change to desirable shades of gray when activated by ultraviolet light, such as that present in sunlight. The photochromic mixtures may be desirably applied to or incorporated within substrates, such as conventional synthetic plastic materials often used for optical elements.

One suitable method of preparing photochromic compounds having the structure of graphic formula II involves reacting a suitable ketone precursor with a metal salt of an alkyne to make an intermediate. The intermediate is then reacted with either an unsubstituted naphthol or a substituted naphthol in the presence of a catalyst. The resultant material is then purified by recrystallization, column chromatography, or a combination of recrystallization and column chromatography.

Some examples of suitable ketone precursors include benzophenone, 4-benzoylbiphenyl, and 4-methoxybiphenylyl phenyl ketone. The metal salt of the alkyne is preferably lithium acetylide and the organic solvent is preferably tetrahydrofuran. The naphthol is preferably 2,6-dihydroxy naphthalene. The catalyst is preferably a catalytic amount of p-toluenesulfonic acid.

One preferred naphthopyran compound, consistent with graphic formula II, is the napthopyran compound that may be represented by graphic formula III below:

the host material. The combination of the composition and host material, as already noted, may be applied to the article or may be used to make the article. Also, compounds represented by graphic formula II and compositions containing one or more compounds represented by graphic formula II may be coated onto the host material, the article, or other suitable substrate.

Polymerized organic materials, such as synthetic polymerized plastic often used to make optical elements, are examples of the host material. Examples of the article include optical elements, such as plano and ophthalmic lenses. Non-exhaustive illustrations of suitable synthetic polymerized plastics suitable for use as the host material include polyacrylate, polycarbonate, polyvinyl alcohol, polyvinyl acetate, polyvinyl chloride, polyurethane, cellulose ester and bis-polyol (allyl carbonate) monomer-based polymer.

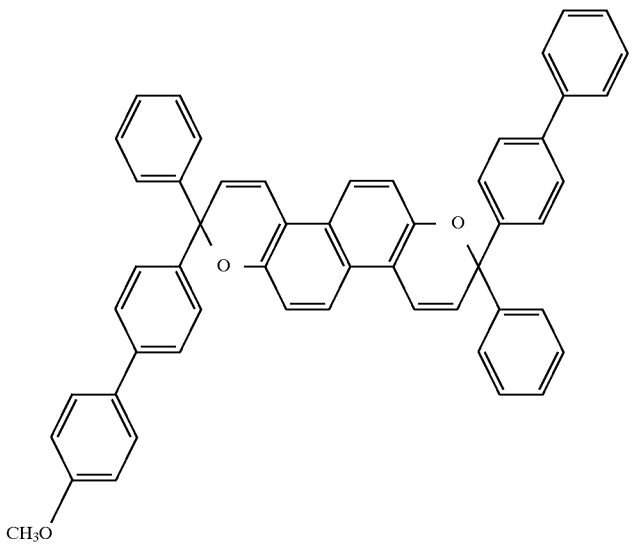

For purposes of the present application, including the description and the claims, it is to be understood that graphical formula III includes all structural isomers of the compound represented by graphical formula III.

When dissolved in chloroform, the compound of graphic formula III, or its structural isomer, unexpectedly exhibits a maximum activated wavelength of absorption of about 500 nanometers when irradiated with ultraviolet light. Additionally, when activated by ultraviolet light, the compound of graphic formula III, or its structural isomer, turns a deep shade of red. Furthermore, the compound of graphic formula III, or its structural isomer, desirably blends with blue-turning photochromic compounds, such as a substituted spiroindolino naphthoxazine, to advantageously make one of the photochromic compound blends that changes to an intense shade of gray when activated by ultraviolet radiation.

The naphthopyran compound represented by graphic formula II may be used in many applications of plastic substrates. For example, compounds represented by graphic formula II may be incorporated into a host material that is applied to an article. Also, compounds represented by graphic formula II may be combined with host material that is used to make the article. Additionally, compositions that contain one or more of the photochromic compounds represented by graphic formula II, such as the previously mentioned photochromic mixtures, may be incorporated into As used in this disclosure, including the description and the claims, the term bis-polyol (allyl carbonate) monomer and similar phrases are intended to mean and include the named monomer or prepolymer and any related monomer series contained therein. Some non-limiting examples of bis-polyol (allyl carbonate) monomers include ethylene glycol bis(allyl carbonate), diethylene glycol bis(2-methylallyl carbonate), diethylene glycol bis(allyl carbonate), propylene glycol bis(2-ethylallyl carbonate), 1-3-propanediol bis(allyl carbonate), 1,3-butanediol bis(allyl carbonate), 1,4-butanediol bis(2,bromoallyl carbonate), dipropylene glycol bis(allyl carbonate), trimethylene glycol bis(2-ethylallyl carbonate), pentamethylene glycol bis(allyl carbonate), and isopropyl idene bisphenol bis(allyl carbonate).

The amount of a particular one of the compounds represented by graphic formula II, or a particular composition containing one of the compounds represented by graphic formula II, that is incorporated into the host material or the coating material is defined, for purposes of this disclosure, as the photochromic amount. The photochromic amount is not critical, provided that a sufficient amount to produce a photochromic effect perceptible to the human eye is used. The photochromic amount often depends on the desired intensity of the color on activation of the particular inventive naphthopyran and on the method of incorporation or application of the particular inventive naphthopyran. Typically, the photochromic amount incorporated into or applied to the host material or incorporated into the coating material ranges from about 0.01 to about 20 percent by weight, based on the weight of the host material or the weight of the coating material, as applicable.

The present invention is more particularly described in the following examples which are intended as illustrations only since numerous modifications and variations within the scope of the general formulation will be apparent to those skilled in the art.

EXAMPLE 1

Step 1

Five grams of benzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be relatively pure diphenyl propargyl alcohol.

Step 2

Two grams of the diphenyl propargyl alcohol obtained in Step 1 were mixed with 1 gram of 2,6-dihydroxynaphthalene in 100 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resulting hexane solution was cooled to yield a recrystallized product. The recrystallized product was shown by nuclear magnetic resonance (NMR) spectroscopy to contain the following relatively pure photochromic compound:

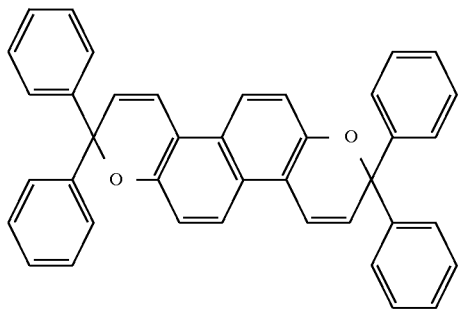

or its structural isomer.

EXAMPLE 2

Step 1

Five grams of 4-benzoylbiphenyl were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectro-scopy showed the resultant material to be relatively pure 4-biphenylyl phenyl propargyl alcohol.

Step 2

Two grams of the 4-biphenylyl phenyl propargyl alcohol obtained in Step 1 were mixed with 0.65 grams of 2,6-dihydroxynaphthalene in 100 milliliters of benzene. Twenty milligrams of p-toluenesulfonic acid were then added and the mixture was stirred under reflux for 8 hours. The resultant mixture was then cooled and washed with 10% aqueous sodium hydroxide. The organic solvent (benzene) was removed using a rotary evaporator. The resulting material was dissolved in hexane and the resultant hexane solution was cooled to yield a recrystallized product. The recrystallized product was shown by nuclear magnetic resonance (NMR) spectroscopy to contain the following relatively pure photochromic compound:

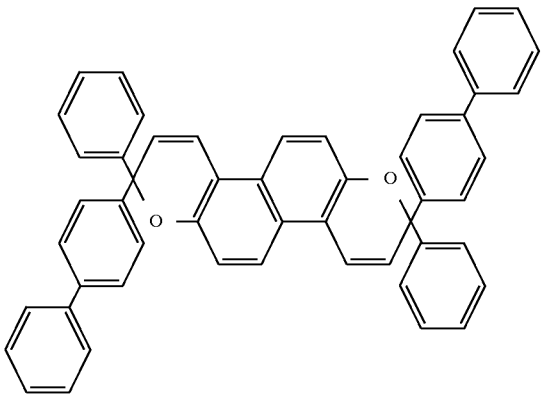

or its structural isomer.

EXAMPLE 3

Step 1

Five grams of 4-methoxybiphenylyl phenyl ketone were placed together with five grams of lithium acetylide in 250 milliliters of tetrahydrofluran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be relatively pure 4-methoxybiphenylyl phenyl propargyl alcohol.

Step 2

Two grams of the 4-methoxybiphenylyl phenyl propargyl alcohol obtained in Step 1 were mixed with 0.63 grams of 2,6-dihydroxynaphthalene in 100 milliliters of benzene. Twenty milligrams of p-toluenesulfonic acid were then added and the mixture was stirred under reflux for 8 hours. The resultant mixture was then cooled and washed with 10% aqueous sodium hydroxide. The organic solvent (benzene) was removed using a rotary evaporator. The resulting material was dissolved in hexane and the resultant hexane solution was cooled to yield a recrystallized product. The recrystallized product was shown by nuclear magnetic resonance (NMR) spectroscopy to contain the following relatively pure photochromic compound:

and a purchased sample of 3,3-diphenyl-3H-naphtho-[2,1b] pyran (identified as Comparative Example 2) were each dissolved in chloroform in separate containers.

Each of these five photochromic compounds that were dissolved individually in separate containers of chloroform were then irradiated with ultraviolet light with a maximum wavelength of 350 manometers and measured for maximum

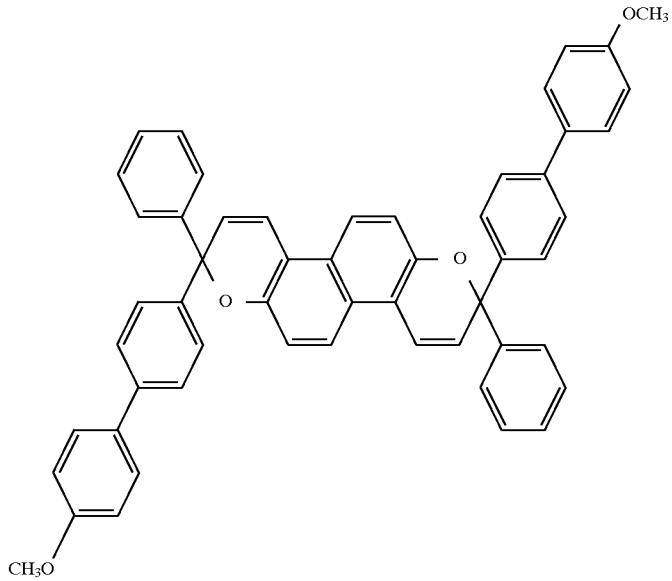

or its structural isomer.

COMPARATIVE EXAMPLE 1

Step 1

Five grams of 4-benzoylbiphenyl were placed together with 5 grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic material was evaporated to obtain a solid material. The solid material was triturated with acetone. Nuclear magnetic resonance (NMR) spectroscopy showed the resultant material to be relatively pure 4-biphenylyl phenyl propargyl alcohol.

Step 2

Two grams of the 4-biphenylyl phenyl propargyl alcohol obtained in Step 1 were mixed with 1.71 grams of 6-methoxy-2-naphthol in 100 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the resultant hexane solution was cooled to yield a recrystallized product. The recrystallized product was shown to be relatively pure 3,3-diphenyl-8-methoxy-3H-naphtho-[2,1b]pyran by nuclear magnetic resonance NMR spectroscopy.

The photochromic compounds formed in Example 1, Example 2, Example 3; the (3,3-diphenyl-8-methoxy-3H-naphtho-[2,1b]pyran) formed in Comparative Example 1;

absorption wavelength, $\lambda_{max}$. The fade time, $T_{1/2}$, was then determined for each of the irradiated compounds. The fade time for of the chloroform-dissolved compounds is defined as the time interval, at room temperature (72° F.), for the absorbance of the activated form of the chloroform-dissolved compound to decrease to one half of the maximum absorbance, after the compound is isolated from the activating source of ultraviolet light. The maximum absorption wavelength and fade time determined for the irradiated photochromic compounds of Examples 1–3 and Comparative Examples 1–2 are presented in Table 1:

TABLE 1

| | $\lambda_{max}$ | $T_{12}$ |
|---|---|---|
| EXAMPLE | | |
| 1 | 490 nm | 10 seconds |
| 2 | 498 nm | 9.5 seconds |
| 3 | 500 nm | 11 seconds |
| COMPARATIVE EXAMPLE | | |
| 1 | 472 nm | 28 seconds |
| 2 | 434 nm | 13 seconds |

Comparative Example 2: Purchased 3,3-diphenyl-3H-naphtho-[2,1b]pyran

The values presented in Table 1 illustrate that the inventive photochromic compounds of Examples 1–3 each have a longer maximum wavelength of activation than that of the 3,3-diphenyl-8-methoxy-3H-naphtho [2,1b]pyran of Comparative Example 1 and the 3,3-diphenyl-3H-naphtho-[2,1b] pyran of Comparative Example 2. The longer maximum wavelengths of activation of the inventive photochromic compounds of Examples 1–3 are desirable characteristics for photochromic compounds. Additionally, the fade times, $T_{1/2}$, of the inventive photochromic compounds of Examples 1–3 range from 9.5 to 11 seconds, which is a desirable range of fade times.

Although the present invention has been described with reference to preferred embodiments, workers skilled in the art will recognize that changes may be made in form and detail without departing from the spirit and scope of the invention.

What is claimed is:

1. A photochromic article comprising a host material and a photochromic amount of a naphthopyran compound, the naphthopyran compound represented by the formula:

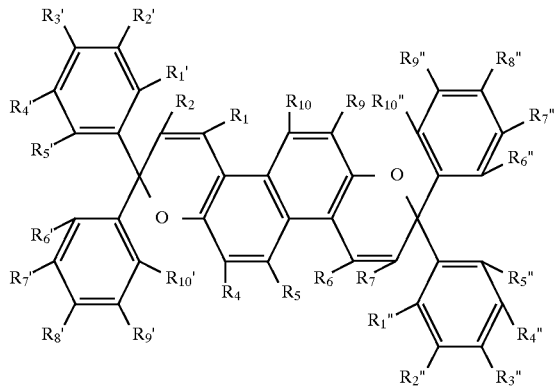

wherein $R_1$, $R_2$, $R_6$, and $R_7$ are each hydrogen;

wherein $R_4$, $R_5$, $R_9$, $R_{10}$, $R_1'$, $R_2'$, $R_3'$, $R_4'$, $R_5'$, $R_1''$, $R_2''$, $R_3''$, $R_4''$, and $R_5''$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino; and wherein $R_6'$, $R_7'$, $R_8'$, $R_9'$, and $R_{10}'$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino, provided that at least one of $R_6'$, $R_7'$, $R_8'$, $R_9'$, $R_{10}'$, $R_6''$, $R_7''$, $R_8''$, $R_9''$, and $R_{10}''$ is selected from the group consisting of unsubstituted phenoxy, substituted phenoxy, naphthyl, naphthoxy, cycloalkyl, furyl, alkoyl, alkoyloxy, aroyl, aroyloxy, nitro, moripholino, piperidino, and piperazino.

2. The photochromic article of claim 1:

wherein $R_1$, $R_2$, $R_6$, and $R_7$, are each hydrogen;

wherein $R_4$, $R_5$, $R_9$, and $R_{10}$ are each selected from the group consisting of hydrogen, $C_1$–$C_2$ alkyl, methoxy and ethoxy;

wherein $R_1'$, $R_2'$, $R_3'$, $R_4'$, $R_5'$, $R_1''$, $R_2''$, $R_3''$, $R_4''$, and $R_5''$ selected from the group consisting of hydrogen, unsubstituted phenyl, substituted phenyl, unsubstituted phenoxy, substituted phenoxy, naphthyl, naphthoxy, alkyl, alkoxy, and cyclic alkyl; and wherein $R_6'$, $R_7'$, $R_8'$, $R_9'$, and $R_{10}'$, $R_6''$, $R_7''$, $R_8''$, $R_9''$, and $R_{10}''$ are each selected from the group consisting of hydrogen, unsubstituted phenyl, substituted phenyl, unsubstituted phenoxy, substituted phenoxy, naphthyl, naphthoxy, alkyl, alkoxy, and cyclic alkyl, provided that at least one of $R_6'$, $R_7'$, $R_8'$, $R_9'$, $R_{10}'$, $R_6''$, $R_7''$, $R_8''$, $R_9''$, and $R_{10}''$ is selected from the group consisting of unsubstituted phenoxy, substituted phenoxy, naphthyl, naphthoxy, and cyclic alkyl.

3. The photochromic article of claim 1 wherein the host material is made of a polymerized organic compound.

4. The photochromic article of claim 3 wherein the polymerized organic compound is selected from the group consisting of polyacrylate, polycarbonate, polyvinyl alcohol, polyvinyl acetate, polyvinyl chloride, polyurethane, cellulose ester, and a polymer of bis-polyol(allyl carbonate) monomer.

5. The photochromic article of claim 1 wherein the naphthopyran compound is present in an amount of from about 0.01 to about 20 percent by weight, based on the weight of the host material.

6. The article of claim 1 wherein the article is an optical element.

7. The article of claim 6 wherein the optical element is a lens.

8. The article of claim 1 wherein the article is a coating for a substrate.

9. The article of claim 1, the article further comprising one or more additional photochromic compounds, the naphthopyran compound and the additional photochromic compounds having different maximum wavelengths of activation.

10. The article of claim 9 wherein the article is a coating for a substrate.

11. The article of claim 1 wherein:

$R_4$, $R_5$, $R_9$, and $R_{10}$ are each selected from the group consisting of hydrogen, alkyl, alkoxy, and cycloalkyl, provided that at least one of $R_4$, $R_5$, $R_9$, and $R_{10}$ is different from another of $R_4$, $R_5$, $R_9$, and $R_{10}$; and wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, substituted phenyl, unsubstituted phenyl, substituted phenoxy, unsubstituted phenoxy, naphthyl, naphthoxy, alkyl, alkoxy, and cycloalkyl, provided that at least one of $R_6'$, $R_7'$, $R_8'$, $R_9'$, $R_{10}'$, $R_6''$, $R_7''$, $R_8''$, $R_9''$, and $R_{10}''$ is selected from the group consisting of unsubstituted phenoxy, substituted phenoxy, naphthyl, naphthoxy, and cycloalkyl.

12. The article of claim 1 wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, substituted phenyl, unsubstituted phenyl, substituted phenoxy, unsubstituted phenoxy, naphthyl, naphthoxy, alkyl, alkoxy, and cycloalkyl, provided that at least one of $R_6'$, $R_7'$, $R_8'$, $R_9'$, $R_{10}'$, $R_6''$, $R_7''$, $R_8''$, $R_9''$, and $R_{10}''$ is selected from the group consisting of unsubstituted phenoxy, substituted phenoxy, naphthyl, naphthoxy, and cycloalkyl.

13. A photochromic article comprising a host material and a photochromic amount of:

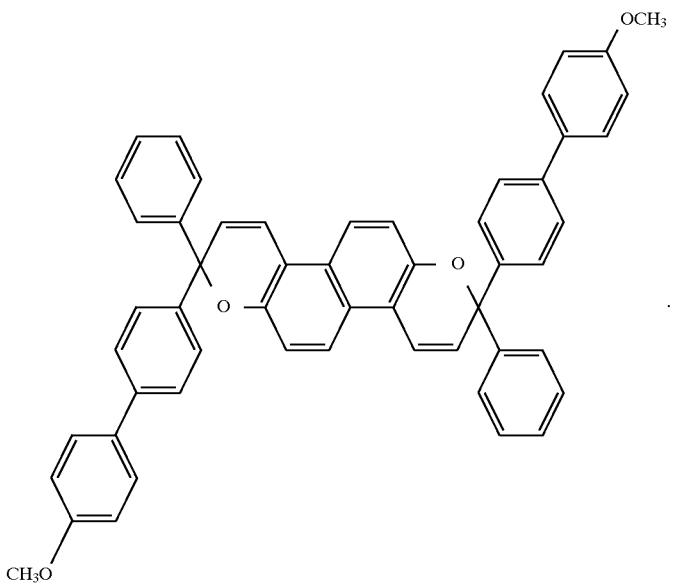

14. A photochromic article comprising a host material and a photochromic amount of a naphthopyran compound, the naphthopyran compound represented by the formula:

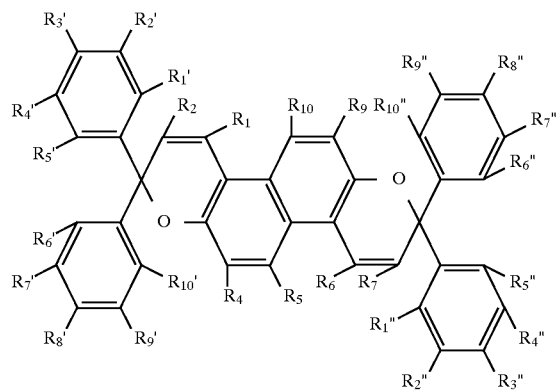

wherein $R_1$, $R_2$, $R_6$, and $R_7$ are each hydrogen;
wherein $R_4$, $R_5$, $R_9$, $R_{10}$, $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino, provided that at least one of $R_4$, $R_5$, $R_9$, and $R_{10}$ is different from another of $R_4$, $R_5$, $R_9$, and $R_{10}$.

15. The article of claim 14 wherein:
$R_4$, $R_5$, $R_9$, and $R_{10}$ are each selected from the group consisting of hydrogen, alkyl, alkoxy, and cycloalkyl, provided that at least one of $R_4$, $R_5$, $R_9$, and $R_{10}$ is different from another of $R_4$, $R_5$, $R_9$, and $R_{10}$; and
wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, unsubstituted phenyl, substituted phenyl, unsubstituted phenoxy, substituted phenoxy, naphthyl, naphthoxy, alkyl, alkoxy, and cycloalkyl.

16. A photochromic article comprising a host material and a photochromic amount of a naphthopyran compound, the naphthopyran compound represented by the formula:

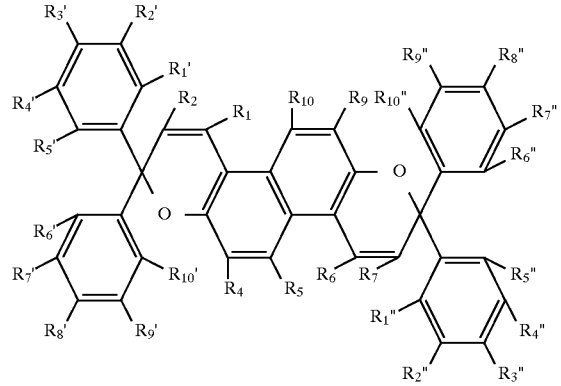

wherein $R_1$, $R_2$, $R_6$, and $R_7$ are each hydrogen;
wherein $R_4$, $R_5$, $R_9$, $R_{10}$, $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino, provided that at least one of $R_4$, $R_5$, $R_9$, and $R_{10}$ is selected from the group consisting of alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino.

17. The article of claim 16 wherein:
$R_4$, $R_5$, $R_9$, and $R_{10}$ are each selected from the group consisting of hydrogen, alkyl, alkoxy, and cycloalkyl, provided that at least one of $R_4$, $R_5$, $R_9$, and $R_{10}$ is selected from the group consisting of alkyl, alkoxy, and cycloalkyl; and
wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, unsubstituted phenyl, substituted phenyl, unsubstituted phenoxy, substituted phenoxy, naphthyl, naphthoxy, alkyl, alkoxy, and cycloalkyl.

18. A photochromic article comprising a host material and a photochromic amount of a naphthopyran compound, the naphthopyran compound represented by the formula:

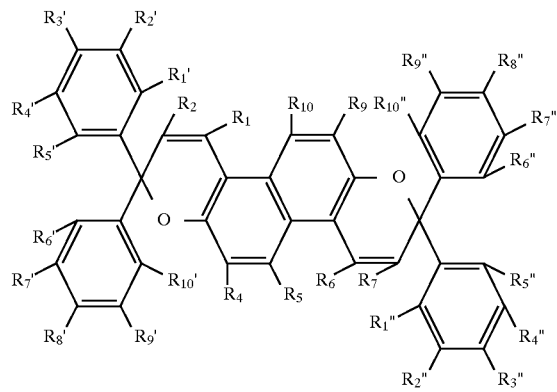

wherein $R_1$, $R_2$, $R_6$, and $R_7$ are each hydrogen;

wherein $R_4$, $R_5$, $R_9$, $R_{10}$, $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino, provided that at least three of $R_1'$, $R_2'$, $R_3'$, $R_4'$, and $R_5'$, at least three of $R_6'$, $R_7'$, $R_8'$, $R_9'$, and $R_{10}'$, at least three of $R_1''$, $R_2''$, $R_3''$, $R_4''$, and $R_5''$, or at least three of $R_6''$, $R_7''$, $R_8''$, $R_9''$, and $R_{10}''$ are selected from the group consisting of alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino.

19. The article of claim 18 wherein:

$R_4$, $R_5$, $R_9$, and $R_{10}$ are each selected from the group consisting of hydrogen, alkyl, alkoxy, and cycloalkyl; and wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, unsubstituted phenyl, substituted phenyl, unsubstituted phenoxy, substituted phenoxy, naphthyl, naphthoxy, alkyl, alkoxy, and cycloalkyl, provided that at least three of $R_1'$, $R_2'$, $R_3'$, $R_4'$, and $R_5'$, at least three of $R_6'$, $R_7'$, $R_8'$, $R_9'$, and $R_{10}'$, at least three of $R_1''$, $R_2''$, $R_3''$, $R_4''$, and $R_5''$, or at least three of $R_6''$, $R_7''$, $R_8''$, $R_9''$, and $R_{10}''$ are selected from the group consisting of unsubstituted phenyl, substituted phenyl, unsubstituted phenoxy, substituted phenoxy, naphthyl, naphthoxy, alkyl, alkoxy, and cycloalkyl.

20. A photochromic article comprising a host material and a photochromic amount of a naphthopyran compound, the naphthopyran compound represented by the formula:

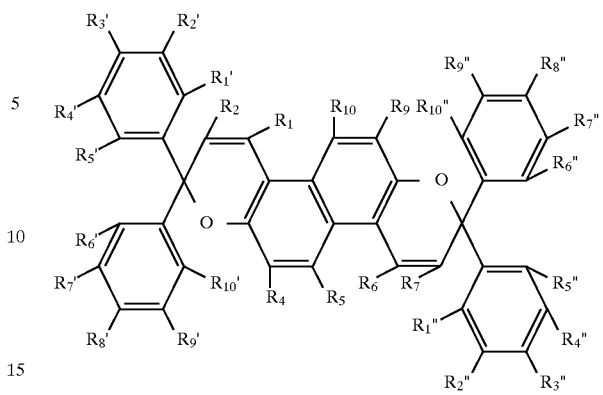

wherein $R_1$, $R_2$, $R_6$, and $R_7$ are each hydrogen;

wherein $R_4$, $R_5$, $R_9$, and $R_{10}$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino; and wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, nitro, morpholino, piperidino, and piperazino, provided that at least one of $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ is selected from the group consisting of unsubstituted phenoxy, substituted phenoxy, naphthyl, naphthoxy, cycloalkyl, furyl, alkoyl, alkoyloxy, aroyl, aroyloxy, nitro, morpholino, piperidino, and piperazino.

21. The article of claim 20 wherein:

$R_4$, $R_5$, $R_9$, and $R_{10}$ are each selected from the group consisting of hydrogen, alkyl, alkoxy, and cycloalkyl; and wherein $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ are each selected from the group consisting of hydrogen, unsubstituted phenoxy, substituted phenoxy, naphthyl, naphthoxy, and cycloalkyl, provided that at least one of $R_1'$, $R_2'$, $R_3'$, $R_4'$, $R_5'$, $R_6'$, $R_7'$, $R_8'$, $R_9'$, $R_{10}'$, $R_1''$, $R_2''$, $R_3''$, $R_4''$, $R_5''$, $R_6''$, $R_7''$, $R_8''$, $R_9''$, and $R_{10}''$ is selected from the group consisting of unsubstituted phenoxy, substituted phenoxy, naphthyl, naphthoxy, and cycloalkyl.

22. A photochromic article comprising a host material and a photochromic amount of a naphthopyran compound, the naphthopyran compound represented by the formula:

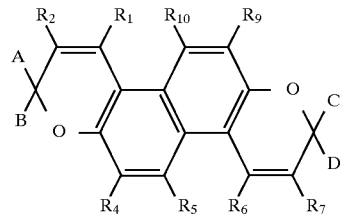

wherein A is

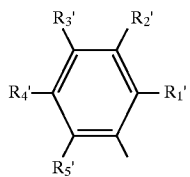

wherein B is

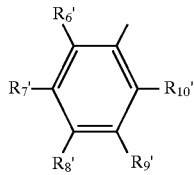

wherein C is

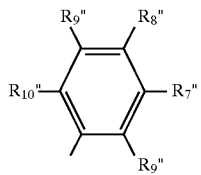

wherein D is

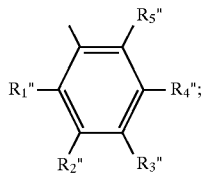

wherein $R_8'$ is

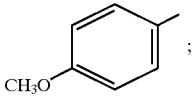

wherein $R_8''$ is

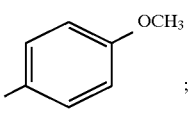

wherein $R_1$, $R_2$, $R_6$, and $R_7$ are each hydrogen;

wherein $R_4$, $R_5$, $R_9$, $R_{10}$, $R_1'$, $R_2'$, $R_3'$, $R_4'$, $R_5'$, $R_1''$, $R_2''$, $R_3''$, $R_4''$, and $R_5''$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino; and wherein $R_6'$, $R_7'$, $R_9'$, $R_{10}'$, $R_6''$, $R_7''$, $R_9''$, and $R_{10}'$ are each selected from the group consisting of hydrogen, alkyl, alkoxy, unsubstituted phenyl, substituted phenyl, unsubstituted phenoxy, substituted phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino, provided that at least one of $R_6'$, $R_7'$, $R_9'$, $R_{10}'$, $R_6''$, $R_7''$, $R_9''$, and $R_{10}''$ is selected from the group consisting of unsubstituted phenoxy, substituted phenoxy, naphthyl, naphthoxy, cycloalkyl, furyl, alkoyl, alkoyloxy, aroyl, aroyloxy, nitro, morpholino, piperidino, and piperazino.

23. The photochromic article of claim 22 wherein the naphthopyran compound is represented by the formula:

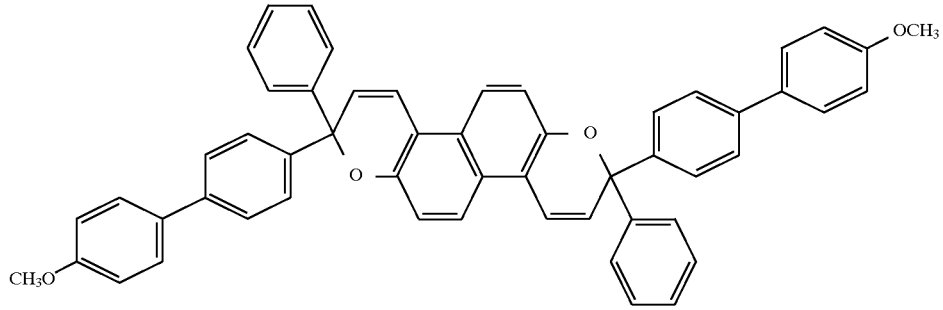

* * * * *

UNITED STATES PATENT AND TRADEMARK OFFICE
CERTIFICATE OF CORRECTION

PATENT NO. : 5,840,926
DATED : NOVEMBER 24, 1998
INVENTOR(S) : FRANK J. HUGHES

It is certified that error appears in the above-identified patent and that said Letters Patent is hereby corrected as shown below:

Col. 11, Line 38, delete "$R_6'$, $R_7'$, $R_8'$, $R_9'$, and $R_{10}'$" insert --$R_6'$, $R_7'$, $R_8'$, $R_9'$, $R_{10}'$, $R_6''$, $R_7''$, $R_8''$, $R_9''$, and $R_{10}''$--

Col. 11, Line 49, delete "moripholino" insert --morpholino--

Col. 11, lines 55-56, insert --are each-- between "$R_5$" and "selected from"

Col. 11, Line 61, delete "$R_6'$, $R_7'$, $R_8'$, $R_9'$, and $R_{10}$, $R_6''$, $R_7''$, $R_8''$, $R_9''$, and $R_{10}''''$", insert --$R_6'$, $R_7'$, $R_8'$, $R_9'$, $R_{10}'$, $R_6''$, $R_7''$, $R_8''$, $R_9''$, and $R_{10}''$--

Col. 17, Lines 21-30, delete

" wherein C is

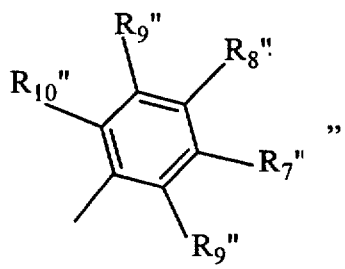

"

UNITED STATES PATENT AND TRADEMARK OFFICE
CERTIFICATE OF CORRECTION

PATENT NO. : 5,840,926

DATED : NOVEMBER 24, 1998

INVENTOR(S) : FRANK J. HUGHES

It is certified that error appears in the above-identified patent and that said Letters Patent is hereby corrected as shown below:

insert --wherein C is

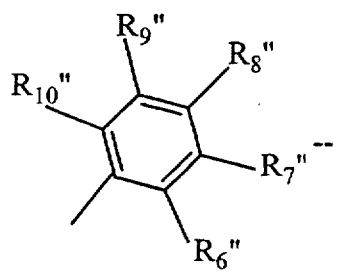

Col. 18, line 27, delete "$R_{10}'''$", insert --$R_{10}''$--.

Signed and Sealed this

Eighteenth Day of January, 2000

Attest:

Q. TODD DICKINSON

Attesting Officer

Commissioner of Patents and Trademarks